United States Patent [19]

Sinha et al.

[11] Patent Number: 5,375,595
[45] Date of Patent: Dec. 27, 1994

[54] APPARATUS AND METHOD FOR NON-CONTACT, ACOUSTIC RESONANCE DETERMINATION OF INTRAOCULAR PRESSURE

[75] Inventors: Dipen N. Sinha; William O. Wray, both of Los Alamos, N. Mex.

[73] Assignee: The Regents of the University of Calif., Alameda, Calif.

[21] Appl. No.: 32,942

[22] Filed: Mar. 17, 1993

[51] Int. Cl.5 .................................................. A61B 3/16
[52] U.S. Cl. ..................................... 128/645; 128/649
[58] Field of Search ............... 128/645, 646, 647, 648, 128/649, 650, 651, 660.01, 660.02, 660.03, 660.06, 661.08; 310/322; 250/227.31, 227.14

[56] References Cited

U.S. PATENT DOCUMENTS

| | | | |
|---|---|---|---|
| 3,882,718 | 5/1975 | Kriebel | 128/648 |
| 4,056,741 | 11/1977 | Hoerz et al. | 310/322 |
| 4,801,799 | 1/1989 | Tromborg et al. | 250/227.31 |
| 4,928,697 | 5/1990 | Hsu | 128/649 |
| 4,945,913 | 8/1990 | Krasnicki et al. | 128/647 |

*Primary Examiner*—Lee S. Cohen
*Assistant Examiner*—Brian M. Green
*Attorney, Agent, or Firm*—Samuel M. Freund

[57] ABSTRACT

Apparatus and method for measuring intraocular pressure changes in an eye under investigation by detection of vibrational resonances therein. An ultrasonic transducer operating at its resonant frequency is amplitude modulated and swept over a range of audio frequencies in which human eyes will resonate. The output therefrom is focused onto the eye under investigation, and the resonant vibrations of the eye observed using a fiber-optic reflection vibration sensor. Since the resonant frequency of the eye is dependent on the pressure therein, changes in intraocular pressure may readily be determined after a baseline pressure is established.

6 Claims, 3 Drawing Sheets

APPARATUS AND METHOD FOR NON-CONTACT, ACOUSTIC RESONANCE DETERMINATION OF INTRAOCULAR PRESSURE

This invention was made with government support under Contract No. W-7405-ENG-36 awarded by the U.S. Department of Energy. The government has certain rights in the invention.

BACKGROUND OF THE INVENTION

The present invention relates generally to the measurement of intraocular pressure, and more particularly to a non-contact, acoustic resonance determination of intraocular pressure.

Glaucoma is an eye disorder that frequently causes blindness. The internal pressure of the eye, or intraocular pressure, increases beyond the normal physiological range and, if not controlled, results in permanent damage to the retina and to the optic nerve. The disorder occurs most frequently in people over forty but may also appear as a congenital condition in children or young adults. There are several types of glaucoma and thousands of people in the U.S. alone suffer from the disease.

The bulb of the eye is composed of segments of two spheres of different sizes separated by a crystalline lens suspended from fibers connected to muscles. The chambers anterior to the lens are filled with aqueous humor and the large cavity posterior thereto is filled by semigelatinous vitreous humor. The intraocular pressure of the eye is maintained by continuous production of aqueous humor, which originates in the chamber behind the iris, flows through the pupil into the anterior chamber between the iris and the cornea, and drains into a channel leading to a network of small veins on the outside of the eye. In glaucoma, either the rate of production of aqueous humor is too high or the rate of drainage is too low causing a pathological increase in the intraocular pressure. The increased pressure is exerted, via the lens, into the vitreous humor, which, in turn, exerts an increased pressure on the retina. This pressure causes collapse of tiny blood vessels which nourish the light-sensitive cells of the retina and the fibers of the optic nerve. Deprived of the blood that provides them with essential oxygen and nutrients, the cells and nerve fibers begin to die causing permanent vision loss.

Presently, the only way to detect glaucoma early is by thorough ophthalmic examination in which a tonometer is used to measure the intraocular pressure. The tonometer requires direct physical contact with the cornea and, consequently, anesthesia is required.

Conservative management of glaucoma involves the use of medication to control the intraocular pressure. The medications involved must be taken for life and regular checkups are necessary. Glaucoma patients must monitor their intraocular pressure frequently to determine if their medication is effective and to detect potentially damaging pressure spikes. The usual practice is to visit the ophthalmologist whenever a pressure measurement is needed. This approach is expensive and discourages continued practice.

Currently, there are no simple, inexpensive pressure measurement devices available to patients for home use. Accordingly, it is an object of the present invention to provide a safe, non-contact apparatus and method for determining intraocular pressure.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for determining intraocular pressure of eyes hereof comprises in combination means for generating bursts of ultrasonic energy having a chosen frequency, said bursts having a chosen duty cycle and a repetition rate within a selected range of frequencies, means for focusing the bursts of ultrasonic energy onto the eye under investigation, and non-contact means for observing the vibrational resonant frequency spectrum thereof resulting from the absorption of energy by the eye from the bursts of ultrasonic energy, whereby the intraocular pressure of the eye may be determined since the resonant frequencies of the eye depend upon the pressure therein.

In a further aspect of the present invention, in accordance with its objects and purposes, the method hereof may comprise the steps of applying bursts of ultrasonic energy having a chosen duty cycle and a repetition rate within a selected range of frequencies to the eye under investigation, and remotely observing the frequency of vibrational resonances induced therein as a result of the incident bursts of ultrasonic energy, whereby the intraocular pressure of the eye may be determined since the resonant frequencies of the eye depend upon the pressure therein.

Benefits and advantages of the present invention include rapid, inexpensive, and simple, non-contact evaluation of intraocular pressure changes.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

Figure 1:
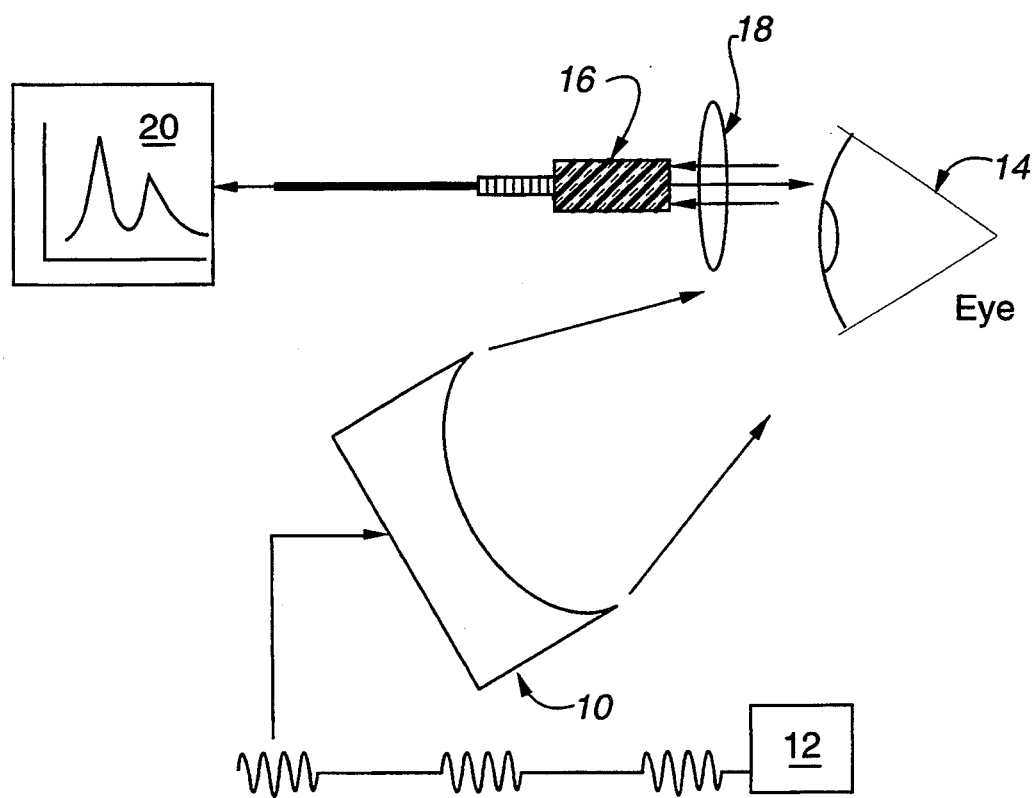
FIG. 1 illustrates the intraocular pressure measuring apparatus of the present invention showing a focusing transducer for applying focused, adjustable duty cycle and repetition rate, pulse bursts of ultrasonic energy to the eye under investigation, and a fiber optic vibration sensor for observing the resonant vibrations therein.

Briefly, the present claimed invention includes an apparatus and method for the non-contact excitation and detection of vibrational resonances in an eye under investigation for the purpose of determining the intraocular pressure therein. An ultrasonic transducer operating at its resonant frequency is amplitude modulated and swept over a range of audio frequencies in which human eyes will resonate. The output therefrom is focused onto the eye under investigation, and the resonant vibrations of the eye observed using a fiber-optic reflection vibration sensor. Since the resonant frequency of the eye is dependent on the pressure therein, changes in intraocular pressure may readily be determined after a baseline pressure is established.

All elastic materials support mechanical vibrations. Moreover, a structure made of an elastic material will exhibit numerous characteristic vibrations whose frequencies depend on the geometry of the structure, the elastic properties of the material, and the manner in which the structure is supported. The cornea is an elastic structure that is attached to the limbus around its periphery and stretched taut by the action of the intraocular pressure exerted by the vitreous humor. The characteristic vibration mode frequencies of the cornea will depend on the elastic properties of the cornea, the density of the vitreous humor, and the intraocular pressure. There is a simple relationship between the resonant vibrational mode frequencies of an eye and the intraocular pressure; that is, the resonant frequency is proportional to the square root of the intraocular pressure. See, e.g., William O. Wray, Elaine D. Best, and Louis Y. Cheng, "Mechanical Model For Radial Keratotomy: Toward A Predictive Capability," Los Alamos National Laboratory report LA-UR-92-1548 (1992), and Robert D. Blevins, *Formulas For Natural Frequency And Mode Shape* (Robert E. Krieger Publishing Company, Malabar, Fla., 1979), p. 229. Therefore, the fractional change in the resonant frequency of an eye is proportional to the fractional change in intraocular pressure. Now, the lowest vibrational mode is predicted to be at about 1 kHz. Ninety-five percent of the population have intraocular pressures between 10.5 and 20.5 mm of Hg, with greater than 20 mm being abnormal, while greater than 25 mm is pathological. A change of 2 mm of mercury corresponds to about 10 Hz. With a resolution of 1 Hz at 1 kHz, about a 0.5 mm of Hg change in intraocular pressure is readily observable. Therefore, one can determine the intraocular pressure by exciting vibrations in the cornea and measuring the frequencies of the characteristic vibration modes. Generally, a single major or fundamental vibration mode is detected along with several other less important higher order modes. The excitation may take two forms; an impulse excitation, or sine-wave continuous excitation. Either may be achieved in a non-contact manner using acoustics. The excitation is followed by the detection of the vibrations to determine the resonant (or dominant) frequency. The detection process can also be accomplished through non-contact optical means. The disadvantage of impulse excitation lies in the fact that determination of the vibration frequency characteristics requires Fast Fourier Transform signal processing which requires sophisticated electronics. Moreover, an impulse excitation approach may subject the eye to high acoustic pressure pulses which may be injurious thereto.

Sine-wave excitation can be accomplished by varying the frequency of excitation with time while vibration amplitudes are monitored in real time. If only a single frequency is to be monitored, phase-lock loop electronics can be employed and the resonant frequency can be hunted and locked-on quickly using feedback from the vibration detection system. The location of the resonant frequency may then be read from a frequency meter. If minor resonances are to be ignored, electronics may be readily designed to automatically tune the excitation frequency to a value such that the amplitude of vibration is maximized. Since the resonances are sharp, frequency determinations can be made quickly.

Resonant frequencies of a pig's eye located outside of the head were found to be between 100 Hz and 1 kHz, higher frequencies being attenuated because of the viscous nature of the aqueous humor and the vitreous body. It should be mentioned that the eye had been refrigerated for about one week prior to measurement, and had lost some of its original internal pressure, resulting in a lower fundamental frequency therefor. For non-contact excitation of the human eye, the simplest approach would be to place an acoustic speaker in front of the eye. However, at the low frequencies involved, the wavelength of sound waves in air is between 30 and 300 cm, making it difficult to focus the energy onto the eye. Moreover, for good efficiency, the speaker must be large giving rise to a significant sound level.

Therefore, a preferred embodiment of the present invention is to use a ultrasonic transducer having a resonant frequency between 20 and 40 kHz. Such transducers are typically less than 2 cm in diameter and are commonly available. Exciting the transducer at its inherent crystal resonant frequency in the burst mode at a chosen repetition rate, provides a way to achieve excitation of an object at this repetition rate. The wave burst is chosen to be between 20 and 100 complete sine-wave cycles. Since the wavelength in air of the resonant crystal frequency is about 1 cm, focusing of this energy onto the eye under investigation is more effectively achieved. Additionally, this frequency is above the human audible range. Recently, 1 MHz resonant frequency transducers for air have become available commercially, and can be effectively employed in the present application. Significantly better focusing ability (about one 1 mm) will permit an eye to be probed selectively in localized areas.

For non-contact monitoring the induced vibrations on the surface of an eye, there are numerous optical techniques available. In a preferred embodiment of the present invention, a commercial fiber-optic reflection vibration sensor was employed to detect vibrations in the pig's eye. With a lens attachment, the fiber optic probe can be situated more than 1 cm away from the surface of the eye in order to detect the microscopic vibrations induced therein. A light emitting diode is used for the light source, since this device may be employed safely when human eyes are investigated, and the light therefrom is not coherent, thereby eliminating undesirable interference patterns characteristic of other laser sources.

Reference will now be made in detail to the present preferred embodiments of the invention, examples of which are illustrated in the accompanying drawings. Turning now to the drawings, FIG. 1 illustrates the intraocular pressure measuring apparatus of the present invention showing a focusing transducer 10 driven by frequency synthesizer 12 for applying focused, adjustable duty-cycle and repetition rate, pulse bursts of ultrasonic energy to the eye under investigation 14, and a fiber optic vibration sensor probe 16 behind optical probe extender optics 18 for observing the resonant vibrations therein and transmitting the amplitude information to sensor electronics and data-acquisition system 20. The optical probe extender houses a precision lens system which can be attached to the probe and permits operation of the present invention at greater distances from the subject eye than would be possible by simply using the bare probe. The extender optics are unnecessary if closer distances are appropriate.

Figure 2:
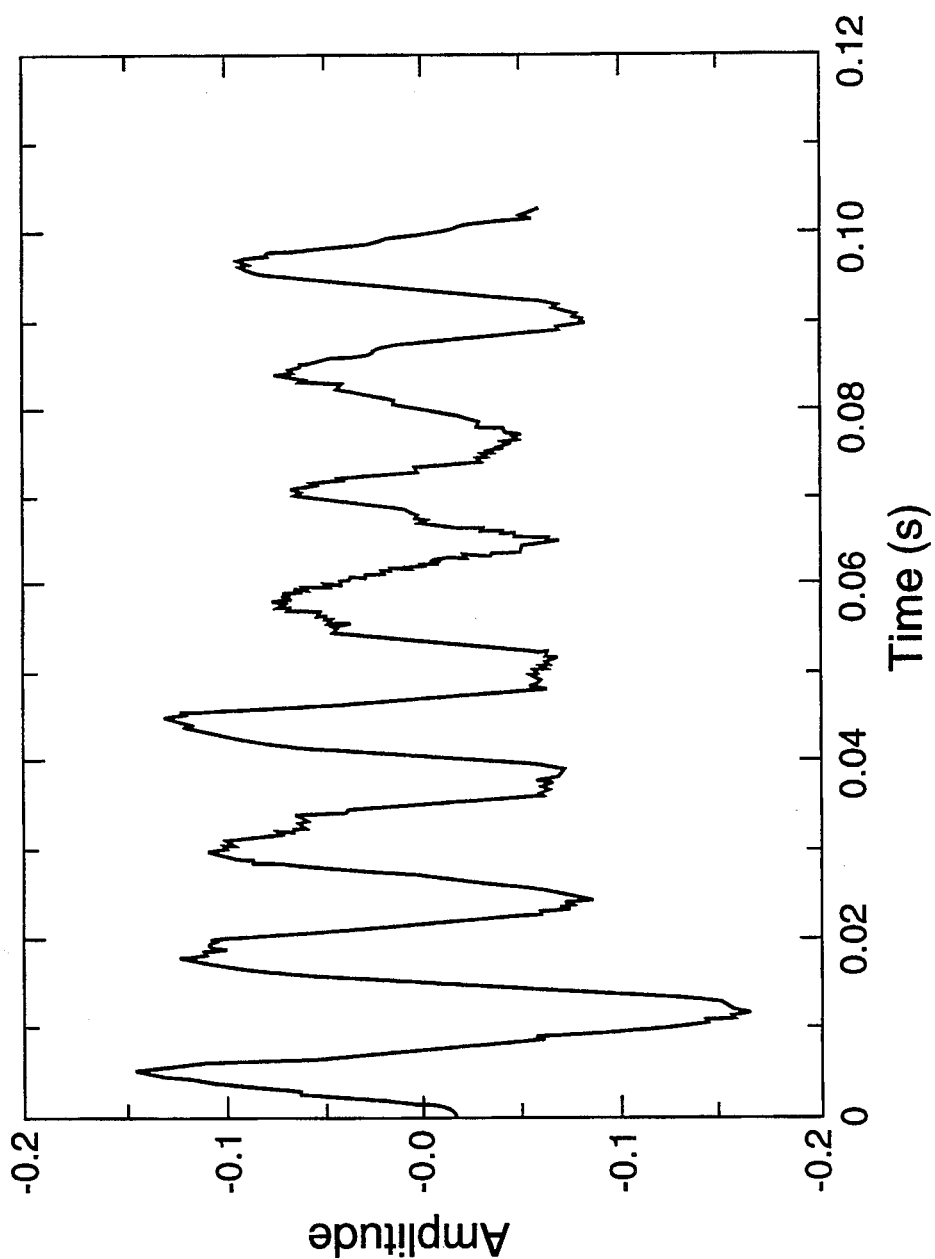
FIG. 2 shows the observed vibrational response (ringing) of a pig's eye as a function of time for an excitation frequency of 77 Hz.

FIG. 2 shows the observed vibrational response (ringing) of a pig's eye as a function of time for an excitation frequency of 77 Hz.

Figure 3:
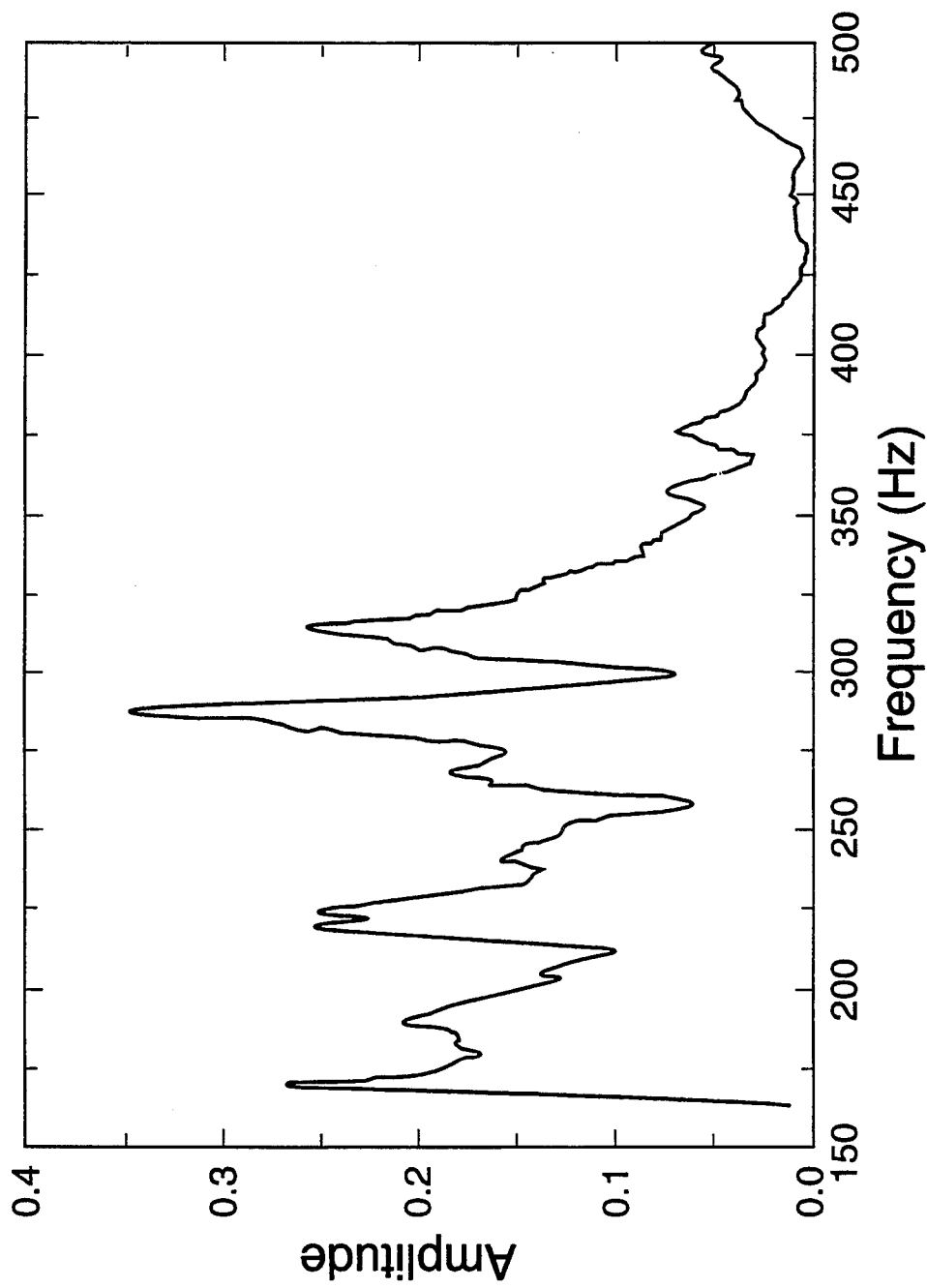
FIG. 3 shows the observed vibrational response of a water-filled balloon as a function of excitation frequency using an apparatus similar to that described in FIG. 1 hereof, except that a speaker was used in place of the focusing transducer identified therein.

FIG. 3 shows the observed, non-contact vibrational response of a water-filled balloon as a function of excitation frequency using an apparatus similar to that described in FIG. 1 hereof, except that a speaker was used in place of the focusing transducer identified therein. A 1 in. diameter balloon was chosen in order to simulate a human eye. Vibrational resonances at smaller frequencies also exist, but were unobservable because of limitations in the apparatus employed. The measurement duration was approximately 10 sec.

The foregoing description of the invention has been presented for purposes of illustration and description and is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for the non-contact determination of intraocular pressure comprising in combination:

a. means for generating a series of trains of periodic ultrasonic sound waves having an adjustable repetition rate and a chosen duty cycle;
   b. means for focusing the generated trains of periodic sound waves onto an eye under investigation; and
   c. non-contact means for measuring the frequencies of resonant vibrations induced in the eye as a result of the interaction of the eye with the focused trains of periodic sound waves.

2. The apparatus as described in claim 1, wherein said means for generating periodic sound waves includes a crystalline transducer operating at its resonant frequency.

3. The apparatus as described in claim 1, wherein said means for measuring resonant vibrations induced in the eye includes a fiber-optic reflection vibration sensor.

4. An apparatus for the non-contact determination of intraocular pressure comprising in combination:

a. means for generating a series of focused trains of periodic ultrasonic sound waves having an adjustable repetition rate and a chosen duty cycle; and
   b. non-contact means for measuring the frequencies of resonant vibrations induced in an eye as a result of the interaction of the eye with the focused trains of periodic sound waves.

5. A method for the non-contact determination of intraocular pressure comprising the steps of:

a. generating a train of periodic ultrasonic sound waves having an adjustable repetition rate and a chosen duty-cycle;
   b. focusing the sound waves produced in said step of generating a train of periodic sound waves onto an eye under investigation; and
   c. measuring the frequency at which vibrational resonances occur in the eye as a result of the interaction thereof with the focused trains of periodic sound waves.

6. The method as described in claim 5, further comprising the step of comparing the frequencies at which resonant vibrations in the eye occur with the resonant frequencies thereof at known intraocular pressures, whereby changes in the intraocular pressure of the eye under investigation can be determined.

* * * * *